(12) United States Patent
Nagano

(10) Patent No.: US 12,089,999 B2
(45) Date of Patent: Sep. 17, 2024

(54) ULTRASONIC DIAGNOSTIC APPARATUS

(71) Applicant: CANON MEDICAL SYSTEMS CORPORATION, Otawara (JP)

(72) Inventor: Gen Nagano, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 54 days.

(21) Appl. No.: 17/651,073

(22) Filed: Feb. 15, 2022

(65) Prior Publication Data

US 2022/0265248 A1    Aug. 25, 2022

(30) Foreign Application Priority Data

Feb. 24, 2021  (JP) ................................. 2021-026970

(51) Int. Cl.
*A61B 8/00*      (2006.01)
*G01S 15/89*    (2006.01)

(52) U.S. Cl.
CPC .............. *A61B 8/54* (2013.01); *A61B 8/4477* (2013.01); *G01S 15/8906* (2013.01)

(58) Field of Classification Search
CPC ....... A61B 8/54; A61B 8/4477; A61B 8/5207; G01S 15/8906; G01S 7/52033; G01S 15/8915

See application file for complete search history.

(56) References Cited

U.S. PATENT DOCUMENTS 6,073,848 A * 6/2000 Giebel ............... G06K 7/10851
                                                        235/462.26
8,568,319 B1 * 10/2013 Kaplan .................... A61B 8/56
                                                        600/407

(Continued)

FOREIGN PATENT DOCUMENTS

| JP | 11-076232 A | 3/1999 |
| JP | 2010-201110 A | 9/2010 |
| JP | 2017-055845 A | 3/2017 |

OTHER PUBLICATIONS

Office Action issued Aug. 6, 2024, in corresponding Japanese Patent Application No. 2021-026970, 3 pages.

*Primary Examiner* — Alexei Bykhovski
(74) *Attorney, Agent, or Firm* — Oblon, McClelland, Maier & Neustadt, L.L.P.

(57) ABSTRACT

An ultrasonic diagnostic apparatus includes an ultrasonic probe, a plurality of detectors, a measurer, and processing circuitry. The ultrasonic probe includes the plurality of transducers, and is configured to transmit an ultrasonic signal to a subject through each of the transducers, and receive, through each of the transducers, a reflected wave signal obtained when the transmitted ultrasonic signal has been reflected from an inside of a body of the subject and returned. Each of the plurality of detectors respectively corresponds to transducers and are configured to detect a reflected wave signal received by the corresponding transducer. The measurer configured to measures a reflected wave signal having an amplitude greater than an amplitude at which at least one of the detectors is saturated when determining a gain of the at least one of the plurality of detectors. The processing circuitry configured to calculate the gain based on the reflected wave signals measured by the measurer and control setting of the gain to the detectors.

7 Claims, 5 Drawing Sheets

(56) References Cited

U.S. PATENT DOCUMENTS

| | | | |
|---|---|---|---|
| 2007/0085606 A1* | 4/2007 | Thomas | G01N 29/36 |
| | | | 330/254 |
| 2013/0289410 A1* | 10/2013 | Cho | B06B 1/0292 |
| | | | 600/459 |
| 2015/0351723 A1* | 12/2015 | Ishihara | G01S 15/8915 |
| | | | 600/443 |
| 2020/0300935 A1* | 9/2020 | Anderson | H01L 21/302 |

\* cited by examiner

ULTRASONIC DIAGNOSTIC APPARATUS

CROSS-REFERENCE TO RELATED APPLICATION

The present application claims priority based on Japanese Patent Application No. 2021-026970, filed Feb. 24, 2021, the content of which is incorporated herein by reference.

BACKGROUND OF THE INVENTION

Field of the Invention

Embodiments disclosed in the present description and drawings relate to an ultrasonic diagnostic apparatus.

Description of Related Art

Conventionally, an ultrasonic diagnostic apparatus including an ultrasonic probe is known. In an ultrasonic diagnostic apparatus, an ultrasonic signal is transmitted from an ultrasonic probe, and the ultrasonic signal is reflected in the body of a subject (patient), returned, and received as an ultrasonic signal (reflected wave signal) by the ultrasonic probe. Then, the analog reflected wave signal received by the ultrasonic probe is processed by an analog circuit such as an amplifier circuit or a filter circuit, and then the analog signal is converted into a digital signal by an analog-to-digital converter (AD converter), and digital processing is performed on the digital signal to generate an image to be presented to an examination practitioner (such as a doctor) in the ultrasonic diagnostic apparatus.

However, if an analog signal is saturated in any of analog circuits in the ultrasonic diagnostic apparatus, the quality of an image to be presented deteriorates. Accordingly, in the ultrasonic diagnostic apparatus, a gain is set for each analog circuit such that a reflected wave signal is not saturated. However, if the gain is lowered such that the reflected wave signal is not saturated, the signal-to-noise (S/N) ratio of the reflected wave signal decreases. Therefore, in the ultrasonic diagnostic apparatus, it is necessary to set an appropriate gain such that the reflected wave signal is not saturated and the S/N ratio does not decrease.

With respect to this, a method of detecting saturation of a reflected wave signal on the basis of an AD-converted signal and a method of switching a gain of an amplifier circuit on the basis of the level of an input signal (that is, a reflected wave signal) of the amplifier circuit are known. However, in conventional methods, sufficient studies have not been conducted on setting of an appropriate gain in a circuit that processes reflected wave signals in an ultrasonic diagnostic apparatus. More specifically, in the method of detecting saturation of a reflected wave signal on the basis of an AD-converted signal, it is impossible to detect an analog circuit in which saturation occurs among analog circuits up to an AD converter. In the method of switching a gain of an amplifier circuit on the basis of the level of an input signal of the amplifier circuit, if saturation occurs in any of analog circuits after the amplifier circuit in the first stage in analog circuits, this saturation cannot be detected.

Furthermore, in recent ultrasonic diagnostic apparatuses, parts in which analog circuits to an AD converter have been integrated are mounted in many cases, and it is more difficult to detect an analog circuit in which saturation of a reflected wave signal occurs.

DETAILED DESCRIPTION OF THE INVENTION

An ultrasonic diagnostic apparatus of an embodiment includes an ultrasonic probe, a plurality of detectors, a measurer, and processing circuitry. The ultrasonic probe includes a plurality of transducers, and is configured to transmit an ultrasonic signal to a subject through each of the transducers, and receive, through each of the transducers, a reflected wave signal obtained when the transmitted ultrasonic signal has been reflected from an inside of a body of the subject and returned. Each of the plurality of detectors respectively corresponds to transducers and are configured to detect the reflected wave signal received by the corresponding transducer. The measurer configured to measures a reflected wave signal having an amplitude greater than an amplitude at which at least one of the detectors is saturated when determining a gain of the at least one of the plurality of detectors. The processing circuitry configured to calculate the gain based on the reflected wave signal measured by the measurer and control setting of the gain in the detectors.

Hereinafter, the ultrasonic diagnostic apparatus of the embodiment will be described with reference to the drawings. The ultrasonic diagnostic apparatus transmits an ultrasonic signal from the ultrasonic probe and receives an ultrasonic signal (reflected wave signal) obtained when the ultrasonic signal is reflected in the body of a subject (patient) and returned through the ultrasonic probe. The ultrasonic diagnostic apparatus detects the reflected wave signal received by the ultrasonic probe, performs analog signal processing on the detected analog reflected wave signal using an analog circuit, and then converts the analog signal into a digital signal through an analog-to-digital converter (AD converter). The ultrasonic diagnostic apparatus performs digital processing on the digital signal through a signal processing circuit to generate an ultrasonic image based on the magnitude of the reflected wave signal, or the like and presents the generated ultrasonic image to an examination practitioner (doctor or the like). Accordingly, the examination practitioner can visually confirm the state of the tissue in the body of the subject.

Figure 1:
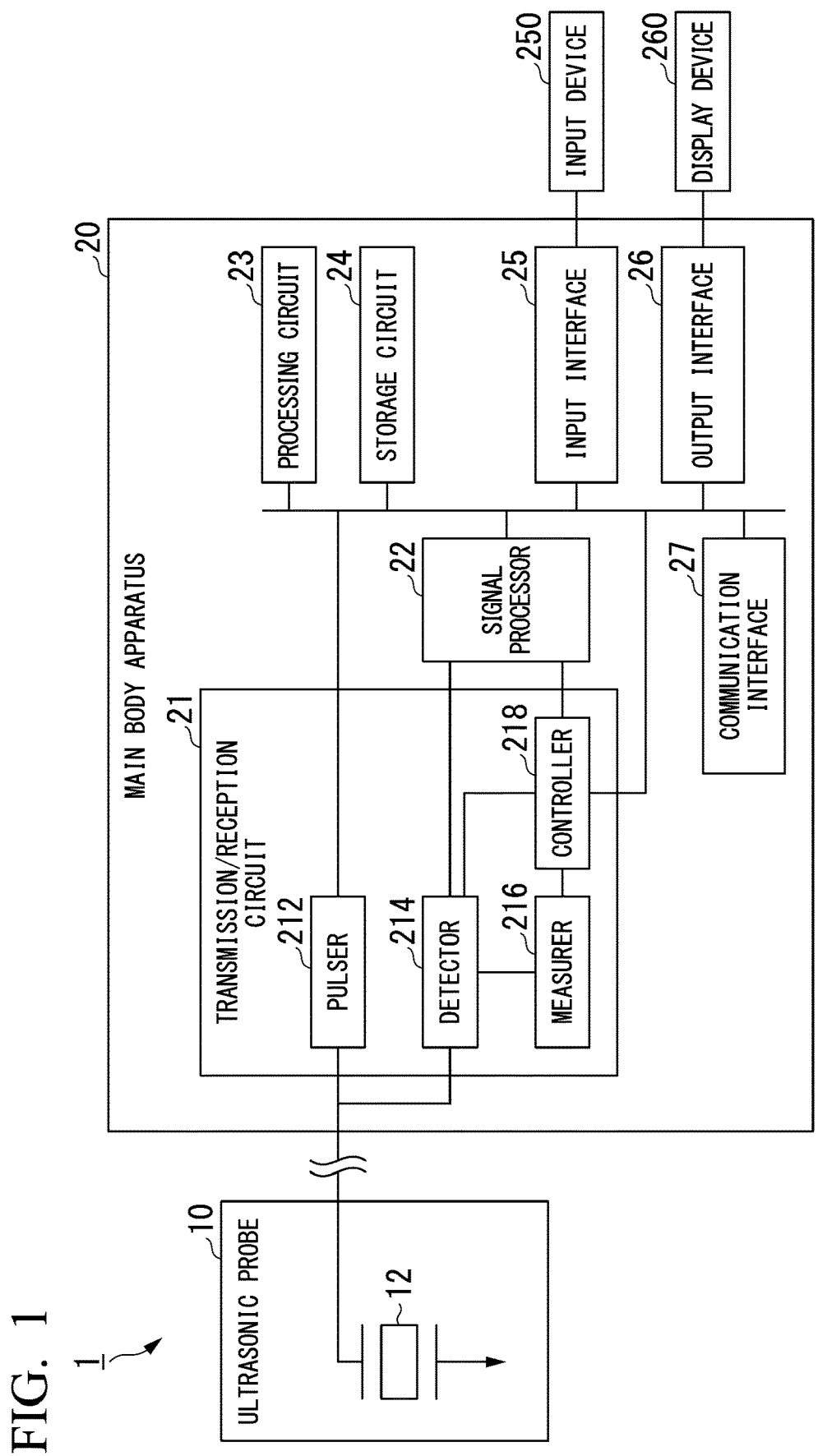
FIG. 1 is a configuration diagram of an ultrasonic diagnostic apparatus according to an embodiment.

FIG. 1 is a configuration diagram of an ultrasonic diagnostic apparatus according to an embodiment. The ultrasonic diagnostic apparatus 1 includes, for example, an ultrasonic probe 10, a main body apparatus 20, an input device 250, and a display device 260. Although FIG. 1 shows a configuration in which the input device 250 and the display device 260 are connected to the main body apparatus 20, the input device 250 and the display device 260 may be configured to be incorporated into the main body apparatus 20.

The ultrasonic probe 10 is used in a state in which it is in contact with or in proximity to the body of a subject. The ultrasonic probe 10 transmits an ultrasonic signal having directivity to the body of the subject, receives a reflected wave signal reflected therefrom, and outputs the reflected wave signal to the main body apparatus 20. The ultrasonic probe 10 includes a plurality of ultrasonic transducers 12. The ultrasonic transducers 12 are, for example, piezoelectric elements such as piezoelectric ceramics. The ultrasonic probe 10 further includes a matching layer provided on each of the ultrasonic transducers 12, a backing material for preventing propagation of ultrasonic signals to the back (opposite to the subject) of the ultrasonic transducer 12, and the like. The ultrasonic probe 10 may be detachable from the main body apparatus 20. The plurality of ultrasonic transducers 12 are arranged in the ultrasonic probe 10 through an arbitrary arrangement method such as in a single row or a two-dimensional arrangement.

The main body apparatus 20 generates an ultrasonic image on the basis of the reflected wave signal output from the ultrasonic probe 10. The main body apparatus 20 includes, for example, a transmission/reception circuit 21, a signal processor 22, a processing circuit 23, a storage circuit 24, an input interface 25, an output interface 26, and a communication interface 27.

The transmission/reception circuit 21 is controlled by a system control function of the processing circuit 23 or the signal processor 22 and performs supply of a driving signal to the ultrasonic probe 10, detection and measurement of a reflected wave signal output from the ultrasonic probe 10, and various types of signal processing on the reflected wave signal. The transmission/reception circuit 21 outputs a detection signal generated through the various types of signal processing to the signal processor 22. The transmission/reception circuit 21 includes, for example, a pulser 212, a detector 214, a measurer 216, and a controller 218.

The pulser 212 is a transmission circuit that supplies a driving signal (transmission pulses) (applies a voltage) to the ultrasonic transducers 12 included in the ultrasonic probe 10. The pulser 212 supplies the driving signal for each channel. The pulser 212 generates a rectangular driving signal corresponding to a pulse signal repeatedly generated at a frequency based on a clock signal output by the processing circuit 23, for example, and supplies the generated driving signal to the ultrasonic probe 10 as a voltage for driving the ultrasonic transducers 12. As a result, in the ultrasonic probe 10, the ultrasonic transducers 12 transmit ultrasonic signals. The pulser 212 includes, for example, a pair of metal-oxide-semiconductor field-effect transistors (MOSFETs) in a complementary configuration and separation diodes connected in series to each MOSFET.

The detector 214 is a reception circuit that detects a reflected wave signal output from the ultrasonic probe 10 in a normal detection operation of the ultrasonic diagnostic apparatus 1. The detector 214 performs various types of signal processing on the detected reflected wave signal for each channel to generate a digital signal representing the magnitude of the detected reflected wave signal and outputs the digital signal to the signal processor 22 as a detection signal. Although predetermined parameters are used when the detector 214 performs various types of signal processing, the parameters can also be set, that is, changed by the controller 218. The detector 214 includes components, such as, for example, a transmit/receive separation switch (hereinafter referred to as "TRSW") 2141, an analog circuit, and an AD converter (hereinafter referred to as "detection ADC") 2146 for each channel.

The TRSW 2141 switches the output destination of a received reflected wave signal to an analog circuit in a period in which the reflected wave signal is assumed to be received (hereinafter referred to as a "reception period"). The reception period is a period required for an ultrasonic signal transmitted by the ultrasonic transducer 12 in the ultrasonic probe 10 to be received as a reflected wave signal reflected by the deepest tissue in the body of a subject for which an ultrasonic image is to be generated. The analog circuit performs analog signal processing on the reflected wave signal output from the TRSW 2141 such that a reflected wave signal having an appropriate signal level is input to the detection ADC 2146. More specifically, the analog circuit performs gain correction on the reflected wave signal output from the TRSW 2141 such that the detection ADC 2146 can convert the reflected wave signal into a digital signal with an effective resolution by making the best use of a dynamic range at the time of analog-to-digital conversion. The analog circuit includes components, such as, for example, a low noise amplifier circuit (hereinafter referred to as "LNA") 2142, a variable gain amplifier circuit (hereinafter referred to as "VGA") 2143, a programmable amplifier circuit (hereinafter referred to as "PGA") 2144, and a low pass filter (hereinafter referred to as "LPF") 2145.

The LNA 2142 amplifies the amplitude of the reflected wave signal output from the TRSW 2141 with low noise on the basis of a set gain. Although the gain of the LNA 2142 is a fixed gain, it can be set or changed by the controller 218. The LNA 2142 outputs the amplified reflected wave signal to the VGA 2143 as an LNA amplified signal. The LNA 2142 is an example of a "first amplifier circuit" in the claims, and the LNA amplified signal is an example of a "first detection signal" in the claims.

The VGA 2143 further amplifies the LNA amplified signal output from the LNA 2142 with a gain changed depending on the time when the reflected wave signal is received. Here, the intensity and reception time of the reflected wave signal vary according to the position (depth) of the tissue in the body of the subject which reflects the ultrasonic signal. That is, a reflected wave signal from the tissue in a shallow part of the body of the subject has a high intensity and a short reception time, whereas a reflected wave signal from the tissue in a deep part of the body of the subject has a low intensity and a long reception time. Further, the frequency attenuation coefficient of the reflected wave signal also varies according to the composition of the tissue (living body) that reflects the ultrasonic signal in the body of the subject. The VGA 2143 amplifies the reflected wave signal (LNA amplified signal) having the varying reception time and attenuation coefficient on the basis of a gain curve in which a gain is set in accordance with the tissue and composition. The VGA 2143 is also referred to as a time gain control (TGC) amplifier circuit. Although the gain curve of VGA 2143 is a fixed gain curve determined for each tissue and composition of a living body, it can be corrected, more specifically, offset by the controller 218. The VGA 2143 outputs the amplified reflected wave signal to the PGA 2144 as a VGA amplified signal. The VGA 2143 is an example of a "second amplifier circuit" in the claims, and the VGA amplified signal is an example of a "second detection signal" in the claims.

The PGA 2144 further amplifies the signal amplified by the VGA 2143 on the basis of a set gain. The gain of the PGA 2144 is switched in response to the state of examination in the ultrasonic diagnostic apparatus 1, such as an operation mode of the ultrasonic diagnostic apparatus 1, a region of a subject to be examined by the ultrasonic diagnostic apparatus 1, and the configuration of the ultrasonic probe 10 connected to the ultrasonic diagnostic apparatus 1. The PGA 2144 outputs the amplified reflected wave signal to the LPF 2145 as a PGA amplified signal.

The LPF 2145 attenuates components having a certain frequency or higher in the PGA amplified signal output from the PGA 2144. The LPF 2145 attenuates high frequency components included in the PGA amplified signal according to a sampling frequency when the detection ADC 2146 performs analog-to-digital conversion. That is, the LPF 2145 attenuates reflected wave signals that are included in the PGA amplified signal and have frequencies exceeding, for example, the Nyquist frequency such that a reflected wave signal having a frequency exceeding the sampling frequency of the detection ADC 2146 is not input to the detection ADC 2146 as high frequency noise, aliasing, or the like. The LPF 2145 is also referred to as an anti-alias filter (AAF). The LPF 2145 outputs the reflected wave signal in which the high frequency components have been attenuated to the detection ADC 2146 as an LPF attenuated signal.

The detection ADC 2146 converts an analog signal on which analog signal processing has been performed by the analog circuit into a digital signal. That is, the detection ADC 2146 performs analog-to-digital conversion on the LPF attenuated signal output from the LPF 2145 to generate a digital signal representing the magnitude of the reflected wave signal. The detection ADC 2146 outputs the generated digital signal to the signal processor 22 as a detection signal. The detection ADC 2146 is an example of a "second analog-to-digital converter" in the claims, and the detection signal is an example of a "second digital signal" in the claims.

The measurer 216 is a reception circuit that measures a reflected wave signal output from the ultrasonic probe 10 in a gain adjustment measurement operation in the ultrasonic diagnostic apparatus 1. The measurer 216 is provided for several channels near the center in which the ultrasonic probe 10 is assumed to receive a reflected wave signal having a high signal level. The measurer 216 is provided in parallel with the detector 214 corresponding to the plurality of ultrasonic transducers 12 arranged at the center of the ultrasonic probe 10. Here, the reflected wave signal measured by the measurer 216 is a reflected wave signal obtained when an ultrasonic signal transmitted in a gain adjustment operation in the ultrasonic diagnostic apparatus 1 is reflected in the body of the subject and returned. The reflected wave signal measured by the measurer 216 is a reflected wave signal having the same amplitude as that of a reflected wave signal output from the ultrasonic probe 10 in a normal detection operation of the ultrasonic diagnostic apparatus 1. In the following description, in order to distinguish between a reflected wave signal detected by the detector 214 and a reflected wave signal measured by the measurer 216, the reflected wave signal measured by the measurer 216 is referred to as a "reflected wave signal for measurement." The measurer 216 amplifies the measured reflected wave signal for measurement, generates a digital signal representing the magnitude of the amplified reflected wave signal for measurement as a measured signal, and outputs the digital signal to the controller 218. The measurer 216 includes components, such as, for example, a changeover switch 2162, an amplifier circuit (hereinafter referred to as "measurement AMP") 2164, and an AD converter (hereinafter referred to as "measurement ADC") 2166.

The changeover switch 2162 switches the connection of a signal line (hereinafter referred to as an "input signal line") for inputting a reflected wave signal to the measurement AMP 2164 according to control of the controller 218. The changeover switch 2162 connects a signal line (hereinafter referred to as an "output signal line") through which the TRSW 2141 included in the corresponding detector 214 outputs a reflected wave signal to the input signal line such that the reflected wave signal for measurement is input to the measurement AMP 2164 during a gain adjustment measurement operation. On the other hand, the changeover switch 2162 separates (disconnects) the output signal line from the input signal line such that the reflected wave signal for measurement is not input to the measurement AMP 2164 at a time other than the gain adjustment measurement operation, such as a normal detection operation. Here, the changeover switch 2162 connects the input signal line to a ground signal line such that a ground level signal is input to the measurement AMP 2164, for example. The changeover switch 2162 is an example of a "switching circuit" in the claims. An operation such as the normal detection operation is an example of a "first operation" in the claims, and the gain adjustment measurement operation is an example of a "second operation" in the claims.

The measurement AMP 2164 amplifies the amplitude of the reflected wave signal for measurement input via the changeover switch 2162 on the basis of a predetermined gain. The measurement AMP 2164 is an amplifier circuit having a large (wide) maximum input amplitude that can be amplified. The measurement AMP 2164 amplifies the amplitude of the input reflected wave signal for measurement to an amplitude that can be input to the measurement ADC 2166. The gain of the measurement AMP 2164 is similar to or lower than the gain of the LNA 2142 included in the detector 214. The measurement AMP 2164 outputs the amplified reflected wave signal for measurement to the measurement ADC 2166 as an AMP amplified signal. The measurement AMP 2164 is an example of a "third amplifier circuit" in the claims, and the AMP amplified signal is an example of a "first measured signal" in the claims.

The measurement ADC 2166 performs analog-to-digital conversion on the AMP amplified signal output from the measurement AMP 2164 to generate a digital signal representing the magnitude of the reflected wave signal for measurement. The measurement ADC 2166 outputs the generated digital signal to the controller 218 as a measured signal. The measurement ADC 2166 may have a larger dynamic range or a higher resolution than the detection ADC 2146. The measurement ADC 2166 is an example of a "first analog-to-digital converter" in the claims, and the measured signal is an example of a "first digital signal" in the claims.

The controller 218 obtains a gain to be set in each amplifier circuit in the analog circuit included in the detector 214 on the basis of the measured signal output from the measurer 216 in the gain adjustment measurement operation in the ultrasonic diagnostic apparatus 1. The controller 218 sets the obtained gain in each corresponding amplifier circuit. More specifically, the controller 218 obtains a gain to be set in the LNA 2142 included in the detector 214 and a gain to be set in the VGA 2143, more specifically, an offset value for offsetting (correcting) a gain curve, and respectively sets the gains in the LNA 2142 and VGA 2143. The start of the gain adjustment measurement operation in the ultrasonic diagnostic apparatus 1 is instructed by, for example, the processing circuit 23 or the input interface 25. The gain set in the LNA 2142 is an example of a "first gain" in the claims, and the gain set in the VGA 2143 is an example of a "second gain" in the claims.

The controller 218 monitors presence or absence of saturation in detection signals output by the detection ADCs 2146 of all channels in the normal detection operation of the ultrasonic diagnostic apparatus 1. Here, the controller 218 acquires the detection signals output by all the detection ADCs 2146 from the signal processor 22. Then, the controller 218 monitors presence or absence of saturation in the detection signals by analyzing the acquired detection signals. When the controller 218 determines that the detection signals have been saturated, the controller 218 outputs information representing this to the processing circuit 23. As a result, the processing circuit 23 can notify the examination practitioner to urge him/her to perform gain adjustment. When the controller 218 receives, for example, an instruction to start the gain adjustment measurement operation from the processing circuit 23 or the input interface 25 in response to this notification, the controller 218 repeats the gain adjustment measurement operation for obtaining the gain to be set in each of the LNA 2142 and the VGA 2143. In response to the instruction to start the gain adjustment measurement operation, the controller 218 may set a gain changed by, for example, a predetermined gain value preset by the examination practitioner or a predetermined gain value set in advance (preset) in the ultrasonic diagnostic apparatus 1 in each of the LNA 2142 and the VGA 2143.

Figure 2:
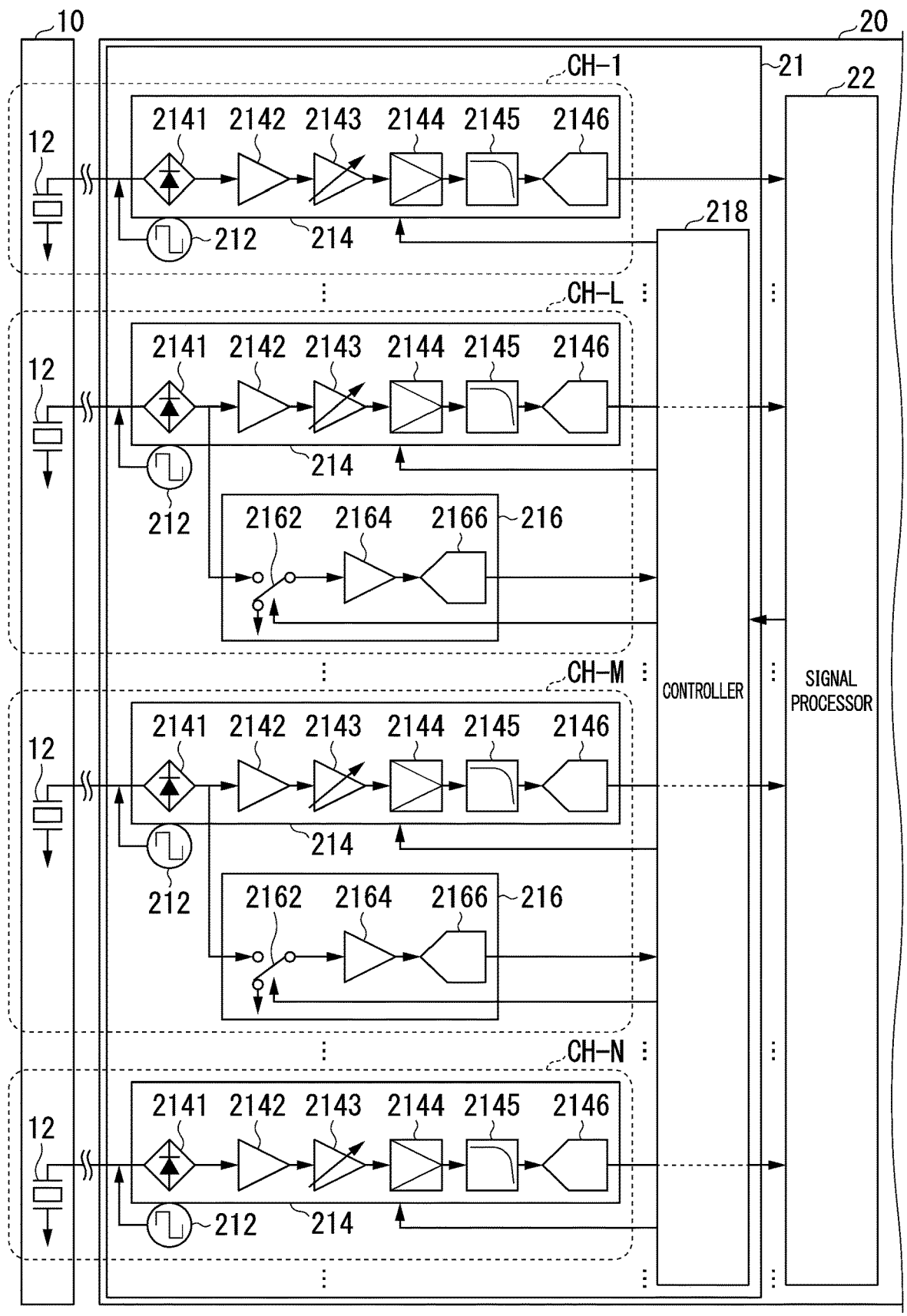
FIG. 2 is a diagram showing an example of a configuration related to a gain adjustment measurement operation in the ultrasonic diagnostic apparatus according to the embodiment.

FIG. 2 is a diagram showing an example of a configuration related to the gain adjustment measurement operation in the ultrasonic diagnostic apparatus 1 according to an embodiment. FIG. 2 is an example of the configuration of the ultrasonic diagnostic apparatus 1 to which an N-channel ultrasonic probe 10 is connected. Accordingly, in the ultrasonic diagnostic apparatus 1 shown in FIG. 2, the pulser 212 and the detector 214 are connected to the ultrasonic transducer 12 of each channel. FIG. 2 also shows connection of components of the TRSW 2141, the LNA 2142, the VGA 2143, the PGA 2144, the LPF 2145, and the detection ADC 2146 included in the detector 214.

In FIG. 2, respective channels (channels CH-1 to CH-N) in the ultrasonic diagnostic apparatus 1 are clearly shown. In FIG. 2, the number or character following "- (hyphen)" after to the code "CH" indicates a channel number in each channel.

In the ultrasonic diagnostic apparatus 1 shown in FIG. 2, the measurers 216 are provided for several channels (channels CH-L to CH-M) near the center. FIG. 2 also shows connection of components of the changeover switch 2162, the measurement AMP 2164, and the measurement ADC 2166 included in the measurer 216.

In the ultrasonic diagnostic apparatus 1 shown in FIG. 2, the controller 218 obtains a gain to be set in the amplifier circuit in the analog circuit included in the detector 214 of each of the channels CH-1 to CH-N on the basis of a measured signal output by the measurer 216 of each of the channels CH-L to CH-M and sets the gain. In the ultrasonic diagnostic apparatus 1 shown in FIG. 2, a configuration in which one controller 218 corresponds to the measurers 216 of the respective channels CH-L to CH-M is shown, but a configuration in which the measurers 216 respectively include controllers 218, the controllers 218, which are included in each of the measurers 216, may obtain and set gains to be set in the respective amplifier circuits in cooperation may be employed.

Figure 3:
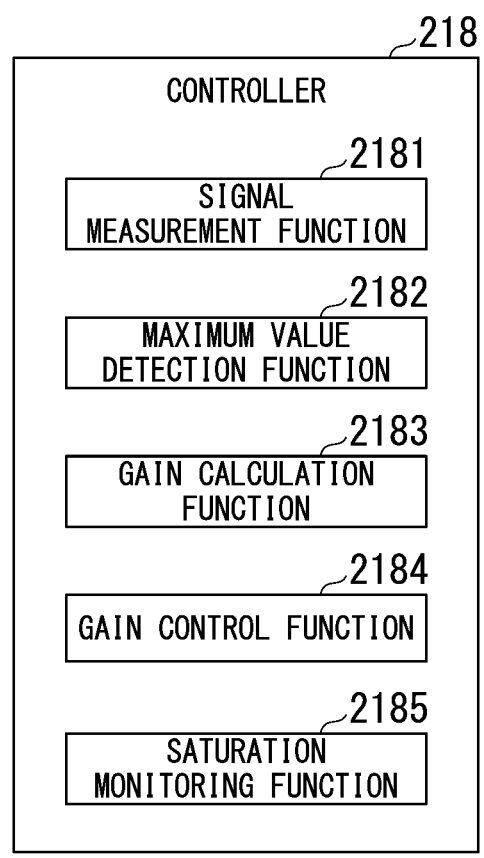
FIG. 3 is a diagram showing an example of a functional configuration of a controller included in the ultrasonic diagnostic apparatus according to the embodiment.

FIG. 3 is a diagram showing an example of a functional configuration of the controller 218 included in the ultrasonic diagnostic apparatus 1 according to an embodiment. The controller 218 executes, for example, a signal measurement function 2181, a maximum value detection function 2182, a gain calculation function 2183, a gain control function 2184, a saturation monitoring function 2185, and the like. The controller 218 realizes these functions by, for example, a hardware processor executing a program stored in a storage device (for example, the storage circuit 24).

The hardware processor means, for example, a circuit (circuitry) such as a central processing unit (CPU), a graphics processing unit (GPU), an application specific integrated circuit (ASIC), a programmable logic device (for example, a simple programmable logic device (SPLD), or a complex programmable logic device (CPLD), or a field programmable gate array (FPGA)). The program may be configured to be directly embedded in the circuit of the hardware processor instead of being stored in the storage device. In this case, the hardware processor realizes the functions by reading and executing the program embedded in the circuit. The hardware processor is not limited to the one configured as a single circuit and may be configured as one hardware processor by combining a plurality of independent circuits to realize each function. The storage device may be a non-transitory (hardware) storage medium. A plurality of components may be integrated into one hardware processor to realize each function. A plurality of components may be incorporated into one dedicated LSI to realize each function. Here, the program (software) may be stored in a storage device (a storage device including a non-transient storage medium) that constitutes a storage device such as a read only memory (ROM), a random access memory (RAM), a semiconductor memory element such as a flash memory, and a hard disk drive (HDD) in advance, or may be stored in a detachable storage medium (non-transient storage medium) such as a DVD or a CD-ROM and installed in a storage device included in the main body apparatus 20 by setting the storage medium in a drive device provided in the main body apparatus 20. The program (software) may be downloaded in advance from another computer device via a network and installed in a storage device provided in the main body apparatus 20. The program (software) installed in the storage device included in the main body apparatus 20 may be transferred to the storage device included in the controller 218 and executed.

The signal measurement function 2181 switches each changeover switch 2162 such that a reflected wave signal for measurement is input to the measurement AMP 2164 in the gain adjustment measurement operation, sets the gain of the LNA 2142 to a maximum gain (hereinafter, "LNA maximum gain"), and causes the pulser 212 to transmit an ultrasonic signal for measurement. Then, the signal measurement function 2181 operates each of the measurement AMP 2164 and the measurement ADC 2166 to acquire, from each measurer 216, a measured signal (digital signal) representing the magnitude of the reflected wave signal for measurement within a reception period output from the TRSW 2141. The signal measurement function 2181 may store each acquired measured signal in, for example, the storage device included in the controller 218 or store it in the storage circuit 24.

The signal measurement function 2181 switches each changeover switch 2162 such that the reflected wave signal for measurement is not input to the measurement AMP 2164 after the measured signal is acquired from the measurer 216 or when the gain adjustment measurement operation ends.

The maximum value detection function 2182 detects the maximum value of the reflected wave signal for measurement on the basis of each measured signal acquired by the signal measurement function 2181. The maximum value of the reflected wave signal for measurement detected by the maximum value detection function 2182 corresponds to the maximum value of a reflected wave signal that is likely to be input to the detector 214, that is, the LNA 2142, in the normal detection operation of the ultrasonic diagnostic apparatus 1. In the following description, the maximum value of the reflected wave signal for measurement detected by the maximum value detection function 2182 is referred to as an "LNA input maximum value." The LNA input maximum value is an example of a "first maximum value" in the claims.

Further, the maximum value detection function 2182 assumes that a gain to be set in the LNA 2142, which is calculated by the gain calculation function 2183, has been set in the LNA 2142, and in this state, obtains an output signal of the LNA 2142 when the detected LNA input maximum value has been input and multiplies the obtained output signal by a gain curve planned when the VGA 2143 performs amplification to obtain the maximum value of an output signal output by the VGA 2143. The planned gain curve is an initial value (which may be a reference value) gain curve that matches the tissue and composition in the body of the subject. As information of the planned gain curve, for example, information stored in the storage device included in the controller 218 may be used or information acquired from the storage circuit 24 on the basis of information of a gain curve set in the VGA 2143, which has been acquired from or designated by the processing circuit 23, may be used. The output signal of the LNA 2142 obtained by the maximum value detection function 2182 is a signal corresponding to the maximum LNA amplified signal output after the reflected wave signal corresponding to the LNA input maximum value is input to the LNA 2142 and amplified in the normal detection operation, that is, output when the LNA input maximum value has passed through the LNA 2142. Then, the maximum value of the output signal of the VGA 2143 obtained by the maximum value detection function 2182 corresponds to the maximum value of the VGA amplified signal that is likely to be output by the VGA 2143 when the maximum LNA amplified signal has been input in the normal detection operation. In other words, it corresponds to the maximum value of an input signal that is likely to be input to the PGA 2144. In the following description, the output signal of the LNA 2142 when the LNA input maximum value obtained by the maximum value detection function 2182 has passed through the LNA 2142 is referred to as a "LNA pass maximum value", and the maximum value of the output signal of the VGA 2143 obtained by the maximum value detection function 2182 is referred to as a "VGA output maximum value." The VGA output maximum value is an example of a "second maximum value" in the claims.

The gain calculation function 2183 calculates the maximum gain of the LNA 2142 through which the LNA input maximum value detected by the maximum value detection function 2182 can pass. Here, the maximum gain of the LNA 2142 calculated by the gain calculation function 2183 is an LNA maximum gain or a gain lower than the LNA maximum gain. In the following description, the maximum gain of the LNA 2142 calculated by the gain calculation function 2183 is referred to as an "LNA maximum pass gain." The LNA maximum pass gain is an example of a "first gain" in the claims.

Further, the gain calculation function 2183 calculates a gain of the VGA 2143 by which the VGA output maximum value obtained by the maximum value detection function 2182 becomes the maximum value of the VGA amplified signal output from the VGA 2143. In other words, the gain calculation function 2183 calculates a gain of the VGA 2143 by which the VGA output maximum value becomes the maximum value of an input signal that can be input to the PGA 2144 (in other words, a limit value of the input signal of the PGA 2144). As for the maximum value of the input signal that can be input to the PGA 2144, for example, maximum value information based on a standard value or the like of the PGA 2144 may be stored in the storage device included in the controller 218, or it may be acquired from or designated by the processing circuit 23 depending on the state of examination in the ultrasonic diagnostic apparatus 1. Then, the gain calculation function 2183 calculates an offset value of the gain curve through which a gain at the time when the VGA amplified signal that is amplified and output reaches the maximum value becomes the calculated gain of the VGA 2143 on the basis of the gain curve of the VGA 2143. In the following description, the offset value of the gain curve of the VGA 2143 calculated by the gain calculation function 2183 is referred to as a "VGA gain offset." The VGA gain offset is an example of a "second gain" in the claims.

The gain control function 2184 sets the LNA maximum pass gain calculated by the gain calculation function 2183 in the LNA 2142 as the gain of the LNA 2142. Further, the gain control function 2184 offsets (corrects) the gain curve of the VGA 2143 with the VGA gain offset calculated by the gain calculation function 2183.

The saturation monitoring function 2185 acquires detection signals output by all detection ADCs 2146 from the signal processor 22 in the normal detection operation, analyzes the acquired detection signals, and monitors presence or absence of saturation in the detection signals output from the detection ADCs 2146 of all channels. For example, the saturation monitoring function 2185 monitors presence or absence of saturation in the detection signals by analyzing waveforms on the time axis represented by the acquired detection signals, and when a state in which the signal level of any of the detection signals has reached an upper limit value continues for a predetermined time or longer, determines that the detection signal is saturated. For example, the saturation monitoring function 2185 monitors presence or absence of saturation in the detection signals by performing frequency analysis on the acquired detection signals, and when rising of any of the detection signals with respect to the fundamental wave of the third harmonic wave of the detection signal is a predetermined level or higher, determines that the detection signal is saturated. A method for determining (detecting) whether or not a detection signal is saturated in the saturation monitoring function 2185 is not limited to the above-mentioned method, and any method may be used as long as it is a suitable method depending on the state of examination in the ultrasonic diagnostic apparatus 1. Upon determining that any of the detection signals is saturated, the saturation monitoring function 2185 outputs information representing this to the processing circuit 23.

By executing such functions, the controller 218 adjusts the gains of the LNA 2142 and the VGA 2143 included in the detector 214 in the gain adjustment measurement operation in the ultrasonic diagnostic apparatus 1. Accordingly, the detection ADC 2146 can output a detection signal obtained by performing analog-to-digital conversion on an LPF attenuated signal output by the LPF 2145 to the signal processor 22 by making the best use of the dynamic range. Further, the controller 218 determines whether or not the detection signal output by the detection ADC 2146 of any channel is saturated in the normal detection operation of the ultrasonic diagnostic apparatus 1. Accordingly, in the ultrasonic diagnostic apparatus 1, the gains of the LNA 2142 and the VGA 2143 included in the detector 214 can be readjusted when any detection signal is saturated. Details regarding processing of adjusting a gain and monitoring presence or absence of saturation in detection signals in the controller 218 will be described later.

Referring back to FIG. 1, the signal processor 22 performs image processing to generate an ultrasonic image that images the state of the tissue in the body of the subject on the basis of the detection signal output from the detector 214 included in the transmission/reception circuit 21. The image processing method in the signal processor 22 is not particularly specified. The signal processor 22 outputs the generated ultrasonic image to the output interface 26 or stores it in the storage circuit 24. The signal processor 22 outputs the detection signal output from the detector 214 to the controller 218 in order to monitor saturation of the detection signal in the controller 218. The signal processor 22 may output the generated ultrasonic image to the controller 218 in order to monitor saturation of the detection signal.

The processing circuit 23 controls the overall operation of the ultrasonic diagnostic apparatus 1. The processing circuit 23 executes, for example, a system control function (not shown) and the like. The processing circuit 23 realizes the system control function that is not shown by, for example, a hardware processor executing a program (software) stored in a storage device (for example, a storage circuit 24). Like the controller 218, the hardware processor of the processing circuit 23 means, for example, a circuit (circuitry) such as a CPU, a GPU, an application specific integrated circuit, or a programmable logic device. For example, the processing circuit 23 executes the system control function that is not shown on the basis of an input operation of the examination practitioner, received through the input interface 25, and controls various operations in the ultrasonic diagnostic apparatus 1. More specifically, the processing circuit 23 instructs the controller 218 to start the gain adjustment measurement operation when the examination practitioner performs an input operation for performing gain adjustment through the input interface 25.

The storage circuit 24 is realized by, for example, a semiconductor memory element such as a ROM, a RAM, or a flash memory, a hard disk drive, an optical disk, or the like. The storage circuit 24 stores setting data (e.g., the gain curve of the VGA 2143, and the like) of components included in the transmission/reception circuit 21, data of a measured signal acquired by the controller 218 (more specifically, the signal measurement function 2181 included in the controller 218), data of an ultrasonic image output from the signal processor 22, and the like. The storage circuit 24 may store in advance the program executed by the controller 218 or the processing circuit 23.

The input interface 25 receives various input operations of the examination practitioner using the ultrasonic diagnostic apparatus 1. The input interface 25 receives an input operation performed by the examination practitioner using an input device 250 such as a mouse, a keyboard, a touch panel, a trackball, a switch, a button, a joystick, a camera, an infrared sensor, and a microphone. The input interface 25 outputs information representing details of the received input operation to the processing circuit 23. For example, when the examination practitioner has performed an input operation for executing gain adjustment, the input interface 25 receives this input operation and outputs information representing that gain adjustment is requested to be executed to the processing circuit 23. In the present description, the input interface 25 or the input device 250 is not limited to those including physical operating components such as a mouse and a keyboard. For example, an electric signal processing circuit that receives an electric signal corresponding to an input operation from an external input device provided separately from the main body apparatus 20 and outputs the electric signal to the processing circuit 23 is also included in an example of the input interface 25.

The output interface 26 provides various types of information to the examination practitioner using the ultrasonic diagnostic apparatus 1. The output interface 26 causes the display device 260 such as a liquid crystal display (LCD), a cathode ray tube (CRT) display, or an organic electroluminescence (EL) display to display, for example, an ultrasonic image output from the signal processor 22 or an ultrasonic image stored in the storage circuit 24 by the signal processor 22. Accordingly, the examination practitioner can confirm the state of the tissue in the body of the subject through the ultrasonic image displayed on the display device 260. The output interface 26 may cause the display device 260 to display a graphical user interface (GUI) image or the like for receiving various input operations executed on the input interface 25 by the examination practitioner.

The communication interface 27 communicates with an external apparatus (not shown) connected via a network such as a local area network (LAN) constructed in a hospital, for example. The external apparatus is, for example, a database apparatus such as a picture archiving and communication system (PACS) that manages data of various medical images or a computerized medical records system that manages electronic health records to which medial images such as ultrasonic images at the time of previous examinations by the ultrasonic diagnostic apparatus 1 have been attached. The external apparatus may be, for example, another medical apparatus such as a computed tomography (CT) apparatus or a magnetic resonance imaging (MRI) apparatus disposed in a hospital.

Figure 4:
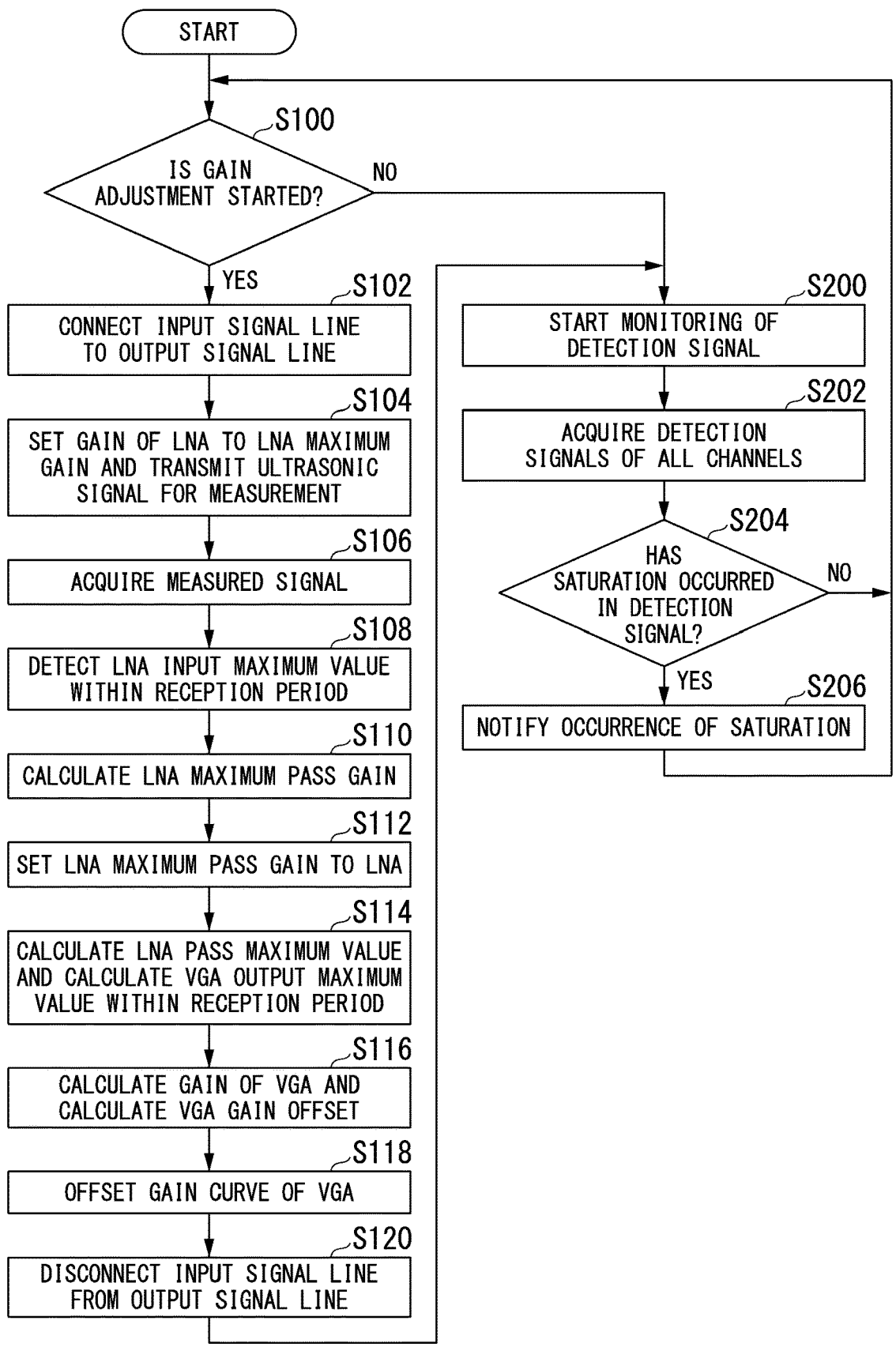
FIG. 4 is a flowchart showing an example of a processing flow in the controller included in the ultrasonic diagnostic apparatus according to the embodiment.

Next, an example of gain adjustment and detection signal monitoring processing in the controller 218 will be described. FIG. 4 is a flowchart showing an example of a processing flow in the controller 218 included in the ultrasonic diagnostic apparatus 1 according to an embodiment. Processing of this flowchart is repeatedly executed while the ultrasonic diagnostic apparatus 1 is activated.

When the ultrasonic diagnostic apparatus 1 is activated, the controller 218 checks whether or not there is an instruction to start the gain adjustment measurement operation (step S100). Here, when an examination practitioner performs an input operation for performing gain adjustment by operating the input device 250 in a state in which the ultrasonic probe 10 is in contact with or in proximity to the body of a subject, the input interface 25 receives this input operation. Then, the processing circuit 23 outputs an instruction to start the gain adjustment measurement operation to the controller 218 on the basis of information of the input operation representing execution of gain adjustment received through the input interface 25. When it is confirmed in step S100 that there is an instruction to start the gain adjustment measurement operation, the controller 218 starts gain adjustment processing.

When gain adjustment processing is started, the signal measurement function 2181 switches the changeover switch 2162 to connect the input signal line of the measurement AMP 2164 to the output signal line of the corresponding TRSW 2141 (step S102). Subsequently, the signal measurement function 2181 sets the gain of the LNA 2142 to the LNA maximum gain and causes the pulser 212 to transmit an ultrasonic signal for measurement (step S104). Then, the signal measurement function 2181 operates each measurement AMP 2164 and measurement ADC 2166 to acquire a measured signal from each measurer 216 (step S106). The signal measurement function 2181 outputs each acquired measured signal to the maximum value detection function 2182.

The maximum value detection function 2182 detects an LNA input maximum value within a reception period on the basis of the measured signals output from the signal measurement function 2181 (step S108). The maximum value detection function 2182 outputs information on the detected LNA input maximum value to the gain calculation function 2183.

The gain calculation function 2183 calculates an LNA maximum pass gain on the basis of the information on the LNA input maximum value output from the maximum value detection function 2182 (step S110). The gain calculation function 2183 outputs information on the calculated LNA maximum pass gain to the maximum value detection function 2182 and the gain control function 2184.

The gain control function 2184 sets the LNA maximum pass gain output from the gain calculation function 2183 in the LNA 2142 (step S112).

The maximum value detection function 2182 calculates an LNA pass maximum value on the basis of the information on the LNA maximum pass gain output from the gain calculation function 2183 and multiplies the calculated LNA pass maximum value by a planned gain curve of the VGA 2143 to calculate a VGA output maximum value within the reception period (step S114). The maximum value detection function 2182 outputs information on the calculated VGA output maximum value to the gain calculation function 2183.

The gain calculation function 2183 calculates a gain of the VGA 2143 by which the VGA output maximum value becomes an input maximum value of the PGA 2144 on the basis of the information on the VGA output maximum value output from the maximum value detection function 2182 and calculates a VGA gain offset on the basis of the calculated gain (step S116). The gain calculation function 2183 outputs the calculated VGA gain offset to the gain control function 2184.

The gain control function 2184 offsets the gain curve of the VGA 2143 on the basis of the information on the VGA gain offset output from the gain calculation function 2183 (step S118).

The signal measurement function 2181 switches the changeover switch 2162 to disconnect the connected input signal line of the measurement AMP 2164 from the output signal line of the corresponding TRSW 2141 (step S120). Accordingly, gain adjustment processing in the controller 218 ends. Here, the controller 218 notifies the processing circuit 23 that gain adjustment processing ends. Accordingly, the processing circuit 23 starts a normal detection operation.

When it is confirmed in step S100 that there is no instruction to start the gain adjustment measurement operation, or when the normal detection operation is started, the controller 218 starts detection signal monitoring processing (step S200).

When detection signal monitoring processing is started, the saturation monitoring function 2185 acquires detection signals output from the detection ADCs 2146 of all channels from the signal processor 22 (step S202). Then, the saturation monitoring function 2185 analyzes the acquired detection signals.

The saturation monitoring function 2185 checks whether or not saturation has occurred in any of the detection signals (step S204). When it is confirmed in step S204 that saturation has not occurred in any of the detection signals, the saturation monitoring function 2185 returns processing to step S100. Accordingly, the controller 218 performs gain adjustment processing again (processing of steps S102 to S120) when there is an instruction to start the gain adjustment measurement operation and continues detection signal monitoring processing on the next detection signal when there is no instruction to start the gain adjustment measurement operation.

On the other hand, when it is confirmed in step S204 that saturation has occurred in any of the detection signals, the saturation monitoring function 2185 outputs (notifies) information representing this to the processing circuit 23 (step S206). Then, the saturation monitoring function 2185 returns processing to step S100.

When the saturation monitoring function 2185 notifies the processing circuit 23 that saturation has occurred in a detection signal, the processing circuit 23 sends a notification urging execution of gain adjustment to the examination practitioner. Then, when the examination practitioner performs an input operation for performing gain adjustment by operating the input device 250 in response to this notification, the input interface 25 receives this input operation, and the processing circuit 23 outputs an instruction to start the gain adjustment measurement operation to the controller 218 on the basis of information on the input operation received by the input interface 25. Accordingly, the controller 218 performs gain adjustment processing (processing of steps S102 to S120) again.

According to such processing, the controller 218 automatically adjusts the gains of the LNA 2142 and the VGA 2143 included in the detector 214 in the ultrasonic diagnostic apparatus 1. Accordingly, in the ultrasonic diagnostic apparatus 1, a signal level can be maximized within a range in which a reflected wave signal is not saturated in the analog circuit included in the detector 214, and the detection ADC 2146 can output a detection signal (digital signal) representing the magnitude of the reflected wave signal to the signal processor 22 by making the best use of a dynamic range. Accordingly, the ultrasonic diagnostic apparatus 1 can generate an ultrasonic image in which deterioration of image quality has been curbed and an S/N ratio has been maximized without causing saturation to occur in signals in the analog circuit involved in detection of a reflected wave signal. Moreover, in the ultrasonic diagnostic apparatus 1, the measurer 216, which is a component for automatic gain adjustment, is provided only in detectors 214 of several channels near the center instead of being provided for the detectors 214 of all channels. Accordingly, the ultrasonic diagnostic apparatus 1 can automatically perform gain adjustment while curbing an increase in the circuit scale and an increase in power consumption.

Furthermore, in the ultrasonic diagnostic apparatus 1, the controller 218 monitors presence or absence of saturation with respect to detection signals output from the detection ADCs 2146 included in the detectors 214 of all channels in the normal detection operation. Accordingly, the ultrasonic diagnostic apparatus 1 can detect saturation of a detection signal due to a change in the signal level of a reflected wave signal which may occur during examination because of, for example, a change (movement) in the position or tissues in the body of a subject, a change (movement) in the position of the ultrasonic probe 10 in contact with or in proximity to the body of the subject, and the like, and if occurrence of saturation in any detection signal is detected, send a notification urging execution of gain adjustment to the examination practitioner.

In an example of processing of the controller 218 shown in FIG. 4, the signal measurement function 2181 connects or disconnects the input signal line to or from the output signal line through the changeover switch 2162 in gain adjustment processing. However, in the ultrasonic probe 10 connected to the main body apparatus 20 to perform examination, the impedance of the ultrasonic probe 10, such as the impedance of the ultrasonic transducer 12, for example, may be lower than an impedance expected in the LNA 2142 because various ultrasonic probes 10 are connected to the main body apparatus 20 in the ultrasonic diagnostic apparatus 1. Further, even in a state in which the input signal line is still connected to the output signal line during the normal detection operation in the ultrasonic diagnostic apparatus 1, that is, a state in which the measurement AMP 2164 is always connected to the output signal line, a certain ultrasonic probe 10 does not have an influence such as a decrease in the signal level of a reflected wave signal received in normal detection, and thus noise due to a non-biological signal or the like may not be generated in a generated ultrasonic image. When such an ultrasonic probe 10 is connected to the main body apparatus 20, the controller 218 can perform gain adjustment processing at regular intervals such as, for example, once in a predetermined frame. That is, the ultrasonic diagnostic apparatus 1 can automatically perform gain adjustment processing without an input operation for performing gain adjustment by an examination practitioner.

Figure 5:
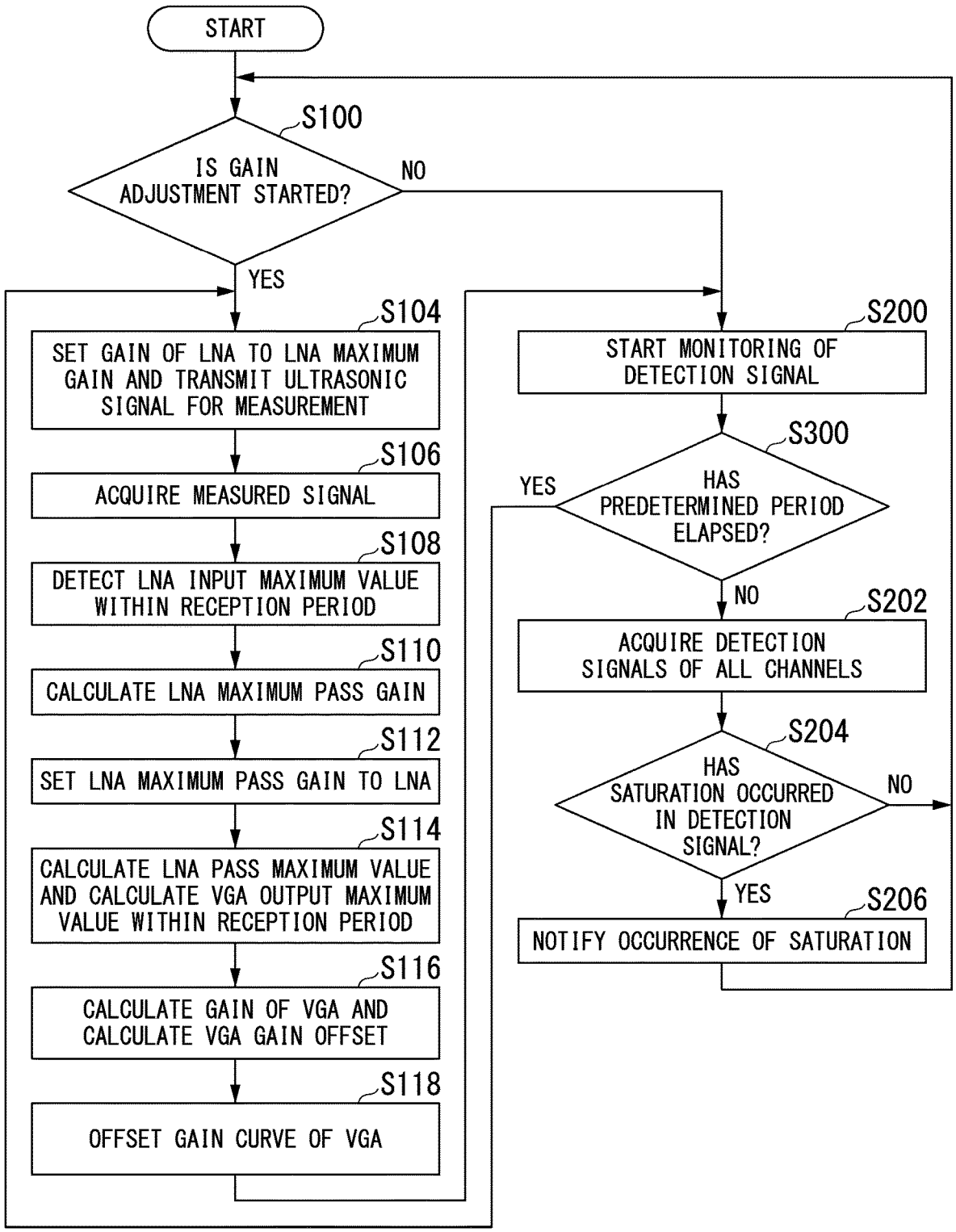
FIG. 5 is a flowchart showing another example of the processing flow in the controller included in the ultrasonic diagnostic apparatus according to the embodiment.

Here, an example of gain adjustment and the detection signal monitoring processing in the controller 218 in this case will be described. FIG. 5 is a flowchart showing another example of the processing flow in the controller 218 included in the ultrasonic diagnostic apparatus 1 according to an embodiment. In the flowchart shown in FIG. 5, the same step number are assigned to the same processing as that of the flowchart shown in FIG. 4. In processing to which the same step numbers are assigned, only different processing contents of processing will be described, and a detailed description of the same processing contents will be omitted. Processing of this flowchart is also repeatedly executed while the ultrasonic diagnostic apparatus 1 is activated.

The controller 218 checks whether or not there is an instruction to start the gain adjustment measurement operation when the ultrasonic diagnostic apparatus 1 is activated (step S100). An input operation of an examination practitioner and processing of the input interface 25 and the processing circuit 23 at this time are the same as processing described at the time of explaining the flowchart shown in FIG. 4. Processing of step S100 is for receiving an input operation for performing gain adjustment by the examination practitioner, in other words, for causing the ultrasonic diagnostic apparatus 1 to execute gain adjustment processing at a desired timing by the examination practitioner. Therefore, when the ultrasonic diagnostic apparatus 1 automatically perform gain adjustment, such as, for example, processing of the first step S100 may be omitted.

When it is confirmed in step S100 that there is an instruction to start the gain adjustment measurement operation (which is not applied when processing of the first step S100 is omitted), the controller 218 starts gain adjustment processing. In processing of the controller 218 when gain adjustment processing is started, only processing of step S102 and processing of step S120 are omitted, and other processing (processing of steps S104 to S118) is the same as processing shown in the flowchart of FIG. 4.

When it is confirmed in step S100 that there is no instruction to start the gain adjustment measurement operation, or when gain adjustment processing in the controller 218 ends, the processing circuit 23 starts the normal detection operation. Then, the controller 218 starts processing of monitoring detection signals (step S200).

When processing of monitoring detection signals is started, the controller 218 checks whether or not a predetermined period has elapsed (step S300). When it is confirmed in step S300 that the predetermined period has elapsed, the controller 218 returns processing to step S104 and performs gain adjustment processing (processing of step S104 to step S118) again.

On the other hand, when it is confirmed in step S300 that the predetermined period has not elapsed, the controller 218 continues processing of monitoring detection signals. Processing of monitoring detection signals is the same as processing (processing of steps S202 to S206) shown in the flowchart of FIG. 4.

According to such processing, in the ultrasonic diagnostic apparatus 1, the controller 218 automatically adjusts the gains of the LNA 2142 and the VGA 2143 included in the detector 214 at regular intervals. Accordingly, in the ultrasonic diagnostic apparatus 1, a signal level can be maximized within a range in which a reflected wave signal is not saturated in the analog circuit included in the detector 214, and the detection ADC 2146 can output a detection signal (digital signal) representing the magnitude of the reflected wave signal to the signal processor 22 by making the best use of a dynamic range. Accordingly, the ultrasonic diagnostic apparatus 1 can generate an ultrasonic image in which deterioration of image quality has been curbed and an S/N ratio has been maximized without causing saturation to occur in signals in the analog circuit involved in detection of the reflected wave signal. Moreover, in the ultrasonic diagnostic apparatus 1, the measurer 216, which is a component for automatic gain adjustment, is provided only for detectors 214 of several channels near the center instead of being provided for the detectors 214 of all channels. Accordingly, the ultrasonic diagnostic apparatus 1 can automatically perform gain adjustment while curbing an increase in the circuit scale and an increase in power consumption.

Further, in the ultrasonic diagnostic apparatus 1, the controller 218 monitors presence or absence of saturation of detection signals output from the detection ADCs 2146 included in the detectors 214 of all channels in the normal detection operation. Moreover, the ultrasonic diagnostic apparatus 1 automatically adjusts the gains of the LNA 2142 and the VGA 2143 included in the detector 214 at regular intervals. Accordingly, the ultrasonic diagnostic apparatus 1 can reduce the frequency at which a detection signal is saturated due to a change in the signal level of a reflected wave signal which may occur during examination because of, for example, a change (movement) in the body position or tissues in the body of a subject, a change (movement) in the position of the ultrasonic probe 10 in contact with or in proximity to the body of the subject, and the like. Further, when the ultrasonic diagnostic apparatus 1 detects occurrence of saturation in any detection signal, the ultrasonic diagnostic apparatus 1 can send a notification urging execution of gain adjustment to the examination practitioner.

However, some ultrasonic probes 10 have a low maximum frequency of a reflected wave signal that is received and output. In this case, the controller 218 can analyze, for example, the maximum frequency of a reflected wave signal or a reflected wave signal for measurement output from the ultrasonic probe 10, using the saturation monitoring function 2185, and on the basis of the analysis result, change a cutoff frequency in the LPF 2145. In this case, the controller 218 can minimize the frequency band of an LPF attenuated signal output from the LPF 2145 to the detection ADC 2146 by setting, for example, the minimum value that is at least twice the maximum frequency to the cutoff frequency of the LPF 2145. Accordingly, the LPF 2145 can output, for example, an LPF attenuated signal in which the noise level of a thermal noise (so-called white noise) included in the entire band of the reflected wave signal has been reduced to the detection ADC 2146, and the detection ADC 2146 can output a measured signal with an improved S/N ratio. Accordingly, the ultrasonic diagnostic apparatus 1 can further improve the S/N ratio of a generated ultrasonic image. Since the operation and processing of the controller 218 in this case can be easily conceived on the basis of the operation and processing of the controller 218 described above, detailed description thereof will be omitted.

As described above, in the ultrasonic diagnostic apparatus 1 of the embodiment, the controller 218 detects the maximum value (LNA input maximum value) of a reflected wave signal that is likely to be input to the LNA 2142 included in the detector 214 on the basis of a measured signal based on a reflected wave signal for measurement output from the measurer 216, calculates the maximum gain (LNA maximum pass gain) of the LNA 2142 that the detected maximum value can pass, and sets the maximum gain in the LNA 2142. Further, in the ultrasonic diagnostic apparatus 1 of the embodiment, the maximum value (VGA output maximum value) of an output signal output by the VGA 2143 in a case where the output signal of the LNA 2142 when the maximum value of the reflected wave signal has been input has been passed is obtained, a gain of the VGA 2143 by which the maximum value of a VGA amplified signal output by the VGA 2143 becomes the obtained maximum value of the output signal is calculated, and the gain curve of the VGA 2143 is offset (corrected). In other words, in the ultrasonic diagnostic apparatus 1 of the embodiment, the controller 218 simulates a reflected wave signal that passes through the LNA 2142 and the VGA 2143 included in the detector 214 on the basis of a measured signal based on a reflected wave signal for measurement output by the measurer 216, obtains the maximum value thereof, and determines gains to be set in the LNA 2142 and the VGA 2143 on the basis of the obtained maximum value. Accordingly, the ultrasonic diagnostic apparatus 1 of the embodiment can maximize a signal level within a range in which a reflected wave signal detected in the normal detection operation is not saturated, curb deterioration of image quality based on a detection signal (digital signal) converted by making the best use of the dynamic range of the detection ADC 2146, and present an ultrasonic image with a maximized S/N ratio to an examination practitioner. Further, in the ultrasonic diagnostic apparatus 1 of the embodiment, the controller 218 can monitor occurrence of saturation in detection signals of all channels in the normal detection operation, and when occurrence of saturation in any detection signal is detected, send a notification urging execution of gain adjustment to the examination practitioner. Accordingly, in the ultrasonic diagnostic apparatus 1 of the embodiment, the examination practitioner can more suitably perform an examination. Moreover, in the ultrasonic diagnostic apparatus 1 of the embodiment, the function of determining gains set in the LNA 2142 and the VGA 2143 and the function of monitoring occurrence of saturation in detection signals are realized while curbing an increase in the circuit scale and an increase in power consumption.

In the ultrasonic diagnostic apparatus 1 of the embodiment, the measurer 216 is provided for several channels near the center. However, the measurer 216 may be provided for, for example, one central channel. In this case, the changeover switch 2162 included in the measurer 216 may be configured such that it can connect the input signal line of the measurement AMP 2164 to the output signal lines of the TRSWs 2141 included in the detectors 214 of several channels near the center. Then, the controller 218 may sequentially switch the output signal lines connected to the input signal line by the changeover switch 2162 in the gain adjustment measurement operation. Even with this configuration, it is possible to set gains suitable for the LNA 2142 and the VGA 2143. In this case, the configuration of the measurer 216 and the operation and processing of the controller 218 can be easily conceived on the basis of the configuration of the measurer 216 and the operation and processing of the controller 218 described above, and thus a detailed description thereof is omitted.

According to at least one embodiment described above, it is possible to set appropriate gains in circuits (at least 2142 and 2143) that perform processing on a reflected wave signal in an ultrasonic diagnostic apparatus (1) by including an ultrasonic probe (10) that includes the plurality of transducers (12), transmits an ultrasonic signal to a subject through each of the transducers, and receives, through each transducer, a reflected wave signal obtained when the transmitted ultrasonic signal has been reflected from the inside of the body of the subject and returned, a plurality of detectors (214) that correspond to the respective transducers and detect reflected wave signals received by the corresponding transducers, a measurer (216) capable of measuring a reflected wave signal having an amplitude greater than an amplitude at which at least one detector is saturated at the time of determining a gain of at least one of the plurality of detectors, and a controller (218) that obtains the gain on the basis of the reflected wave signal measured by the measurer and controls setting of the gain to the detector.

Although several embodiments have been described, these embodiments are presented as examples and are not intended to limit the scope of the invention. These embodiments can be implemented in various other forms and various omissions, substitutions, and modifications can be made without departing from the gist of the invention. These embodiments and modifications thereof are included in the scope and gist of the invention and included in the invention and the equivalent scope thereof described in the claims and the equivalent scope thereof.

What is claimed is:

1. An ultrasonic diagnostic apparatus, comprising:
an ultrasonic probe that includes a plurality of transducers, and is configured to transmit an ultrasonic signal to a subject through each of the plurality of transducers, and receive, through each of the plurality of transducers, a reflected wave signal obtained when the transmitted ultrasonic signal has been reflected from an inside of a body of the subject and returned;
a plurality of detectors that respectively correspond to the plurality of transducers and are configured to detect the reflected wave signals received by the corresponding plurality of transducers;
a measurer configured to measure a reflected wave signal having an amplitude greater than an amplitude at which at least one of the plurality of detectors is saturated when determining a gain of the at least one of the plurality of detectors; and
processing circuitry configured to calculate the gain based on the reflected wave signal measured by the measurer and control setting of the gain to the plurality of detectors, wherein each of the plurality of detectors includes at least a first amplifier circuit and a second amplifier circuit, the first amplifier circuit being configured to output a first detection signal obtained by detecting the reflected wave signal and amplifying the detected reflected wave signal, and the second amplifier circuit being configured to output a second detection signal obtained by further amplifying the first detection signal, the measurer includes a third amplifier circuit and a switching circuit, the third amplifier circuit being configured to output a first measured signal obtained by measuring a reflected wave signal for measurement output from the ultrasonic probe in a detection operation and amplifying the measured reflected wave signal for measurement, the switching circuit being configured to switch input of the reflected wave signal for measurement to the third amplifier circuit, and the processing circuit is further configured to control the switching circuit such that the reflected wave signal is not input to the third amplifier circuit in a first operation in which the plurality of detectors detect the reflected wave signal, and the reflected wave signal is input to the third amplifier circuit in a second operation of determining a first gain to be set to the first amplifier circuit and a second gain to be set to the second amplifier circuit.

2. The ultrasonic diagnostic apparatus according to claim 1, wherein the measurer further includes a first analog-to-digital converter configured to convert the first measured signal into a first digital signal, and wherein the processing circuit is further configured to calculate the first gain and the second gain based on the first digital signal, and control setting of the first gain and the second gain for each of the first amplifier circuit and the second amplifier circuit.

3. The ultrasonic diagnostic apparatus according to claim 2, wherein the first amplifier circuit is a low noise amplifier circuit configured to allow a signal having a first amplitude to pass, the second amplifier circuit is a variable gain amplifier circuit, and the third amplifier circuit is an amplifier circuit configured to allow a signal having a second amplitude to pass, wherein the second amplitude is larger than the first amplitude.

4. The ultrasonic diagnostic apparatus according to claim 3, wherein the processing circuit is further configured to detect a first maximum value of the reflected wave signal based on the first digital signal, set a maximum gain that allows the detected first maximum value to pass as the first gain, calculate an output signal when the first maximum value has passed through the first amplifier circuit set to the first gain, calculate a second maximum value by multiplying the output signal by a gain curve planned for the second amplifier circuit, and set a gain at which the second maximum value becomes a maximum value of the second detection signal output by the second amplifier circuit as the second gain for correcting the gain curve.

5. The ultrasonic diagnostic apparatus according to claim 2, wherein each of the plurality of detectors further includes at least a second analog-to-digital converter configured to convert the detected reflected wave signal into a second digital signal that represents the magnitude of the reflected wave signal, and wherein the processing circuit is further configured to control measurement of the reflected wave signal and setting of the gain by the measurer based on a result of monitoring the second digital signal of all the plurality of detectors.

6. The ultrasonic diagnostic apparatus according to claim 1, wherein the reflected wave signal is an ultrasonic signal obtained when the ultrasonic signal transmitted by each of the plurality of transducers has been reflected from the inside of the body of the subject and returned, when determining the gain of the plurality of detectors.

7. The ultrasonic diagnostic apparatus according to claim 1, wherein the measurer is provided for each of the plurality of detectors corresponding to transducers arranged at a center of the ultrasonic probe among the plurality of transducers.

* * * * *